(12) United States Patent
Neuberger et al.

(10) Patent No.: US 8,292,935 B2
(45) Date of Patent: Oct. 23, 2012

(54) PHOTONIC DEVICE AND METHOD FOR TREATING CERVICAL DYSPLASIA

(75) Inventors: Wolfgang Neuberger, Labuan (MY); Stefan Spaniol, Bonn (DE)

(73) Assignee: Bistitec Pharma Marketing Ltd, F.T. Lubuan (MY)

( * ) Notice: Subject to any disclaimer, the term of this patent is extended or adjusted under 35 U.S.C. 154(b) by 1363 days.

(21) Appl. No.: 11/897,621

(22) Filed: Aug. 31, 2007

(65) Prior Publication Data

US 2008/0065003 A1 Mar. 13, 2008

Related U.S. Application Data

(60) Provisional application No. 60/844,052, filed on Sep. 12, 2006.

(51) Int. Cl.
*A61N 5/06* (2006.01)
(52) U.S. Cl. ............... 607/88; 607/89; 607/138; 606/17
(58) Field of Classification Search ............. 607/88–93, 607/116, 138; 606/13–19
See application file for complete search history.

(56) References Cited

U.S. PATENT DOCUMENTS

| | | | | |
|---|---|---|---|---|
| 5,478,339 A * | 12/1995 | Tadir et al. | ...... | 606/15 |
| 5,964,749 A * | 10/1999 | Eckhouse et al. | ...... | 606/9 |
| 7,184,614 B2 * | 2/2007 | Slatkine | ...... | 385/5 |
| 7,935,139 B2 * | 5/2011 | Slatkine | ...... | 607/88 |
| 2010/0076526 A1 * | 3/2010 | Krespi et al. | ...... | 607/88 |

FOREIGN PATENT DOCUMENTS

WO WO93/21842 A1 11/1993
WO WO94/15666 A1 7/1994

* cited by examiner

*Primary Examiner* — Ahmed Farah
(74) *Attorney, Agent, or Firm* — Bolesh J. Skutnik; BJ Associates

(57) ABSTRACT

A method and device used for treating body cells affected by abnormal cell growth or by oncogenic viruses. In particular the invention relates to photonic device for treating gynecological problems comprising at least one light source incorporated into the irradiation head or into the hand piece or as a external unit connected by light guide. The light source used in the photonic device has a LED, Laser or lamps. This photonic device is used for treating a subject having unwanted cell proliferation, example dysplasia of the portio and/or cervix with Photodynamic therapy (PDT). The advantage of using LED device is, for its radiation safety, cost effectiveness and is easy to handle compared to laser system. A drug applicator is also described which is employed for homogenously application of photoactive drug in the affected area.

9 Claims, 4 Drawing Sheets

PHOTONIC DEVICE AND METHOD FOR TREATING CERVICAL DYSPLASIA

DOMESTIC PRIORITY UNDER 35 USC 119(e)

This application claims the benefit of U.S. Provisional Application Ser. No. 60/844,052 filed Sep. 12, 2006, entitled "Photonic Device and Method for Treating Cervical Dysplasia" by Wolfgang Neuberger and Stefan Spaniol, which is incorporated by reference herein.

BACKGROUND OF THE INVENTION

1. Field of the Invention

This present invention concerns a device and Photodynamic therapy (PDT) method for treating cancerous conditions in humans. In particular, this invention relates to high power Light Emitting Diode (LED) based photonic device for treating hyper-proliferative cell conditions related to gynecology problems in humans and animals.

2. Invention Disclosure Statement

The photodynamic therapy (or PDT) method involves administration of photosensitizer followed by application of light energy. Photo activated photosensitizer generates photo oxidation for tissue destruction. PDT is used for treating hyper-proliferative cell conditions in humans and animal. The main differences between PDT and other tumour therapies, like chemotherapy and radiotherapy, are its localized and controllable effectiveness. The limited penetration of light into tissue can be used to treat superficial tumors without damaging delicate structures situated below the diseased area, which are often at risk in radiotherapy.

PDT has been clinically used to treat metastatic breast cancer, bladder cancer, lung carcinomas, oesophageal cancer, basal cell carcinoma, malignant melanoma, ocular tumors, head and neck cancers, and other types of malignant tumors. Because PDT is selective in destroying abnormal cells that have absorbed more of the photosensitizer, than normal cell can, thus it can successfully be used to kill malignant tissue with less effect on surrounding cells in critical areas.

Two of the parameters controlling the efficacy of PDT are the intensity and total amount of the light received by the treated tissue. Because of scattering of light by the tissue a field of diffuse light is received by the tissue, consisting of the original incident light plus light scattered from other irradiated areas. Irradiation with appropriate wavelength for a given photosensitizer may be administered by variety of methods.

PDT methods provide a minimally invasive procedure for treating gynecological problems without needing anesthesia. Dysplasia is abnormal growth of the cells. Dysplasia of cervix and portio is a term used to describe the appearance of abnormal cells on the surface of the cervix, the lowest part of the uterus. It can range from mild to moderate or severe depending on the spread of the abnormal cells. While dysplasia itself does not cause health problems, it is considered to be a precancerous condition. When left untreated, dysplasia sometimes progresses to an early form of cancer known as cervical carcinoma in situ, and eventually to invasive cervical cancer. Dysplasia occurs in females aged 15 and over, and most often in those in 25 to 35 age group. Experimental and epidemiologic data suggest that certain subtypes of human papilloma virus (HPV) play an etiologic role in the development of cervical carcinoma by transforming epithelial cells into precancerous cells.

The reported incidence of cervical dysplasia every year is approximately between 250,000 and 1 million women in the United States alone. Most dysplasia cases can be cured with early diagnosis, proper treatment and follow-up. Without treatment, 30% to 50% may progress to invasive cancer.

Presently available treatment methods include medication, electro-cauterization, cryosurgery, laser vaporization, and surgery. In cryotherapy the cervix is cooled to sub zero temperature thus damaging the cells by freezing them. The main advantage of this method is it is simple and inexpensive. A main disadvantage is, it cannot freeze the abnormal cell seated deep below and are thus left behind untreated. Thus is not suitable to treat large and severe conditions of dysplasia.

Loop excision is another conventional method wherein the tissue is removed by a loop of wire. Also known as LEEP (loop electrosurgical excision procedure), loop excision uses a fine wire loop with electrical energy flowing through it to remove the abnormal area of the cervix. Cramping is common during the procedure, and light bleeding is expected.

In the cone biopsy method a cone of tissue is removed from in and around the cervix either by surgery or by using a laser. This procedure requires anesthesia and is carried out in a surgical setting. Light bleeding and discomfort is common after the procedure.

Hysterectomy is another option but this can be done in women who do not want to bear children in future. It has the lowest recurrence rate of any treatment, but it is a major surgical procedure. Even after a hysterectomy the dysplasia can come back on the vagina, so it is essential to get regular pap smears even if a hysterectomy is done. Most of all it is not suitable for women in child bearing age group.

In laser therapy, carbon dioxide laser is used to vaporize the abnormal cells. The laser is directed through the colposcope so that normal cells are not affected and the laser is directed precisely at the affected region. Healing after laser treatment is much faster than after freezing because dead tissue is not left behind. Studies using the latest techniques of laser treatment are showing lower failure rates with the laser than with freezing. Another important advantage is that the cervix usually heals with the squamo-columnar junction visible, so that future evaluation is easily carried out.

The major disadvantage of the laser therapy is that it requires sophisticated equipment, and most gynecologists do not have a laser in their office. It is much more expensive to do laser if it has to be done in the hospital. All these methods are not very effective for treating invasive cancers.

Although most of these methods are effective to some extent in treating dysplasia, unfortunately, it can be detrimental to fertility and normal childbearing process. In an attempt to encircle all abnormal tissue and the transformation zone of the endocervical lining, the cervix may loose the ability to withstand the weight load of a normal gestation towards term. A solution to the incompetent cervix is surgical cerclage, which again carries high risk of failure, infection and detriment to future fertility. Additionally ablative techniques may leave behind residual microscopic abnormal tissue. This predicament is usually addressed by additional ablative treatments, further increasing damage to the cervix.

In WO 94/15666A1 a light emitting diode source for PDT application had been shown. Here a LED based light device with 660 nm wavelength, having a fluid cooling system has been disclosed. The device is designed to produce large surface area illumination, that can be used to treat certain dermatological problem and for other applications. Similarly in WO 93/21842A1 a high power light emitting diodes is presented for PDT applications. In this invention LED based apparatus are used for activating photosensitizers at a single wavelength band and uniform power density. The cancerous and other undesirable tissues or cells are directly illuminated using a suitably positioned LED device. Another example of LED based light delivery device for uniform surface illumination of tissues or cells is presented in U.S. Pat. No. 5,698,866. Most of the LED based light applicators used in the prior art are designed for surface illumination and for treating dermatological problems. None of these devices are suitable for treating the cervical dysplasia.

In the present invention a photonic based device is presented which is less expensive, compact and easier to handle compared to laser. The present invention aims at providing a suitably designed applicator and a PDT method for treating cervix and other portion of the body where abnormal cells growth is reported. The present method overcomes the drawback reported in current treatment methods.

OBJECTIVES AND BRIEF SUMMARY OF THE INVENTION

It is an objective, of the present invention to provide a suitable light source as a photoirradiation device for treating gynecological related problems.

It is yet another objective, of the present invention to provide a high power LED based device which can fulfill the spectral and power needs for medical application.

It is also yet another objective of the present invention to provide a photonic device suitable for uniformly irradiating the entire area of a cavity.

It is still another objective, of the present invention to implement an array of multiple integrated LED directly into the irradiation head or into the hand piece or as an external source.

It is one other objective, of the present invention to provide a drug applicator to apply the photosensitizer homogenously to hyperproliferative tissues in portio and cervix regions to be treated with PDT.

It is also the objective of the present invention to use gel formulation of photoactive substance.

It is further objective, of the present invention to have a light guide to connect the external light source to irradiation head.

Briefly stated, present invention relates to a method and device used for treating body cells affected by abnormal cell growth or by oncogenic viruses. In particular the invention relates to photonic device for treating gynecological problem comprising at least one light source incorporated into the irradiation head or into the hand piece or as a external unit connected by light guide. The light source used in the photonic device includes but is not limited to LED, laser and lamps. This photonic device is used for treating a subject having unwanted cell proliferation, example dysphasia of the portio and/or cervix with Photodynamic therapy (PDT). The advantage of choosing an LED or lamp device is, for its radiation safety, cost effectiveness and its ease of handling compared to a laser system. A drug applicator is also described which is employed for homogenously application of photoactive drug in the affected area.

The above and other objects, features and advantages of the present invention will become apparent from the following description read in conjunction with the accompanying drawings.

DETAILED DESCRIPTION OF PREFERRED EMBODIMENTS

For effective PDT, light sources must satisfy several requirements. They must emit a suitable wavelength or band of wavelengths for activating the photosensitizer. It should be focusable to areas that cannot be directly irradiated. Main problems faced in treating certain types of cancer are the lack of availability of equipment which can access the diseased area in question. A photonic device suitable for PDT application in gynecological problem is provided in this invention.

Figure 5:
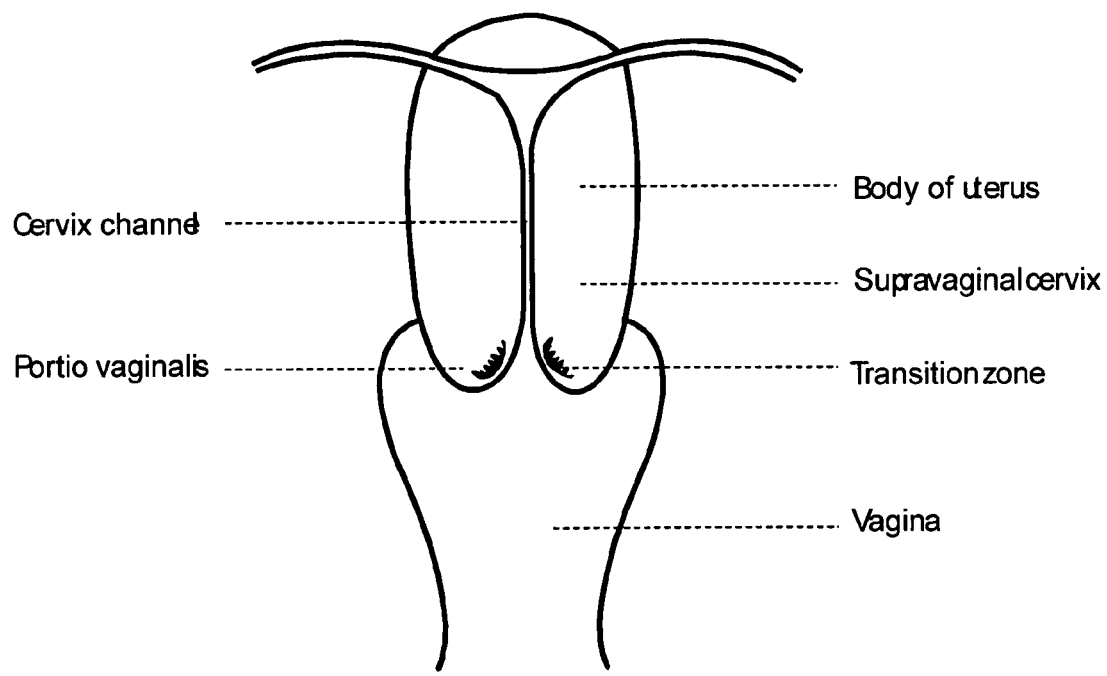
FIG. 5—diagrammatic representation of cervix and portio.

The present invention provides an effective PDT based treatment modality for precancerous and cancerous conditions of portio and cervical regions. FIG. 5 illustrates anatomy of uterine cervix. Certain oncogenic human papilloma virus (HPV) can infect the cells in the cervix and portio region inducing dysplasias that can develop into cancerous conditions when left untreated. In the US alone there are around half a million patients surgically treated per year for colonization of the portio.

The region of the cervix, where the columnar epithelium has been replaced by the new metaplastic squamous epithelium is referred to as the transformation zone (FIG. 5). Identifying the transformation zone is important as almost all manifestations of cervical carcinogenesis occur in this zone.

PDT and light application systems based on laser and fiber optic are successfully used to treat dysplasias of portio and cervix. In the PDT method, the photosensitizer is administrated to the patient systemic or locally. After a certain time interval-Drug-Light-Interval, (DLI), light of an appropriate wavelength matching the absorption spectra of the photosensitizer is applied to the site to activate the photosensitizer and bring about photo destruction. Currently lasers are used for irradiation in combination with properly designed light destruction device that are connected to laser unit via an optical fiber. Major disadvantage of using laser is that it requires sophisticated equipment, that which are costly and requires highly skilled professionals and more over need to ensure proper laser radiation protection.

The use of PDT for gynecological related problems, although not extensive, has been encouraging. Preferential Photofrin uptake and retention as demonstrated by fluorescence has been reported in both dysplasia and cervical carcinomas. Primary and recurrent vaginal cancers, cervical, and ovarian tumors have been treated by PDT.

LED have limited emission spectrum band with high efficiency but at low cost. LED is a solid state electronic device capable of emitting light when an electric current is passed through the device. LED offers an effective alternative to expensive laser system. LED are comparatively simpler device that operates over much wider ranges of current and temperature.

In one of the embodiment of light emitting diodes (LED) are used as light source in photonic device. Light from an LED is administered using a device capable of delivering the requisite power to the treatment area. High power LED based device can be employed to fulfill the spectral and power needs for different medical application. In the present invention light source used for irradiation includes but not limited to LED, laser and lamps.

The LED based photonic device of present invention is powerful enough to reach a power density of around 100 mW/cm² in the desired wavelength range. LED array in this device can be incorporated into irradiation head, hand piece and or as an external unit. When incorporated into hand piece or irradiation head, risk of eye or other organs being exposed to harmful radiation is avoided. This invention is further illustrated by the description of the figures.

Figure 1:
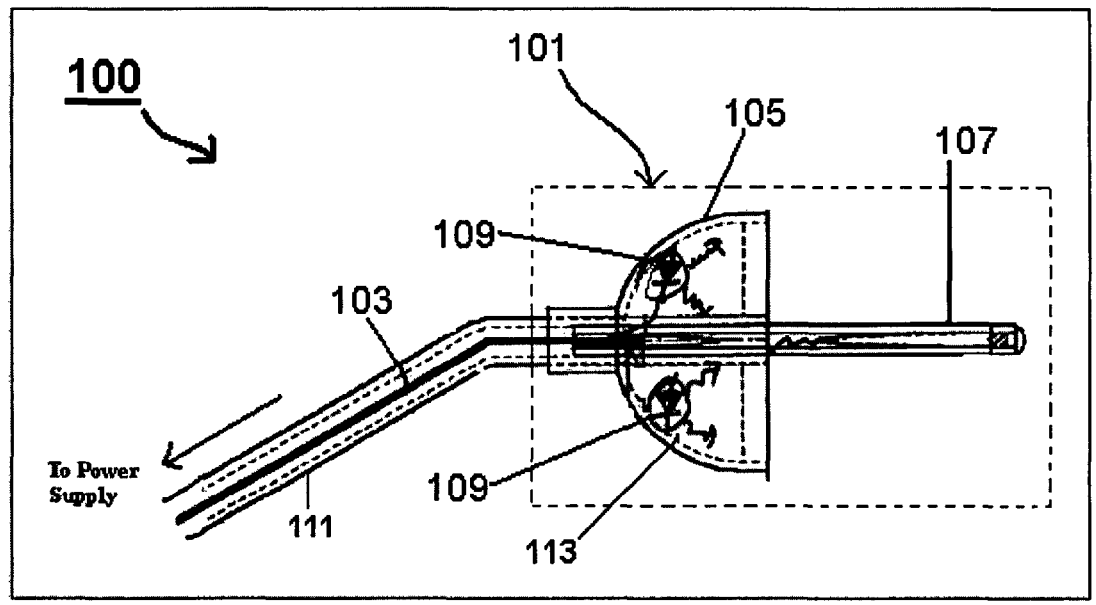
FIG. 1—illustrates a photonic device with LED incorporated into the irradiation head.

In the treatment of gynecological dysplasia, FIG. 1 illustrates one of the embodiments of the present invention where the LEDs are incorporated directly into a photonic device 100 shaped to provide a uniform illumination to the treatment areas in and around the cervix. Photonic device 100 is connected to a power supply, not shown, by electric wires 103 through handle 111. An illumination head 101 has a semi spherical reflector 105 that can be flexible or rigid with a reflective/scattering surface 113; onto which an LED array 109 is incorporated. A cylindrical tube 107 mounted within reflector 105 is transparent or partially reflective and also acts to position and center the illumination head 101. Illuminator head 101 is shaped appropriately for insertion into the cervical regions and to irradiate the cervix, portio and transition zone uniformly. In the present invention, radiation from the LED array 109 is shielded from the operator by reflector 105. A portion of the radiation from LED array 109 enters into tube 107 and is transmitted from the distal end of tube 107 by means of internal reflection sources, not shown. Further, there may be LEDs solely for the purpose of transmitting radiation through tube 107 either directly into tube 107 or by means of optical fibers attached thereto. Illumination head 101 is connected to the power supply by a connector, not shown, to handle 111.

Figure 2:
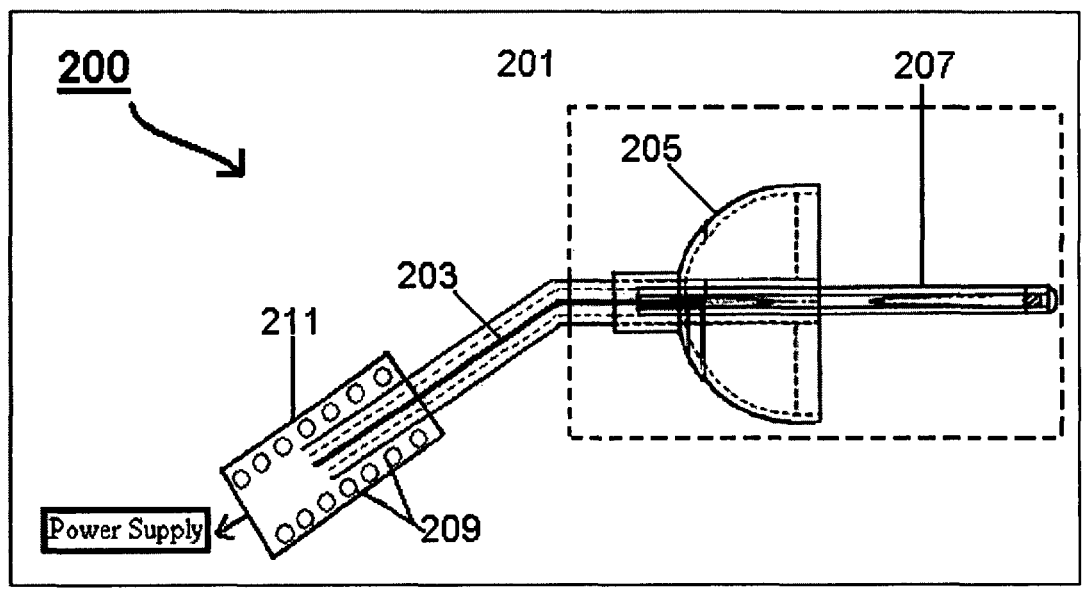
FIG. 2—shows the LED being incorporated into the headpiece of the photonic device FIG. 3—depicts the photonic device with LED as an external Unit.

FIG. 2 schematically represents another embodiment of the present invention where an LED array 209 is included in to hand piece 211 of the photonic device 200. LED arrays 209 is arranged into the hand piece 211 which is connected to the illumination head 201 by a light guide 203. The illuminator head 201 consists of a reflector 205 with a cylindrical tube 207 designed for insertion into the cervical region for uniform irradiation of precancerous and cancerous cells. In this embodiment, the radiation from LED array 209 travels down guide 203 and enters into tube 207. In order for the radiation to leave tube 207, multiple scattering sources, for example, may be encased within tube 207. Further, the density of these scattering sources may vary to provide the appropriate radiation to reflector 205 and to the distal section of tube 207 located beyond the reflector 205.

Figure 3:
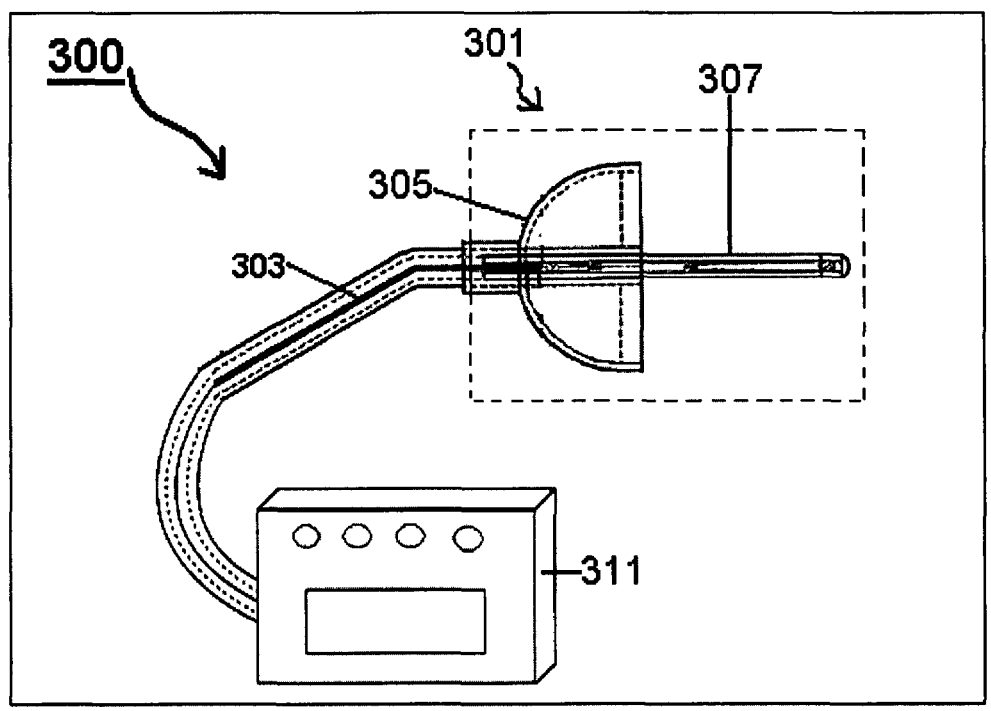

FIG. 3 illustrates yet another embodiment of the present invention. Gynecological device 300 consists of an external LED unit 311 which is connected to the illumination head by light guide 303. Illumination head 301 consists of a reflector 305 and cylindrical tube 307 as similarly described in FIG. 2.

Figure 4:
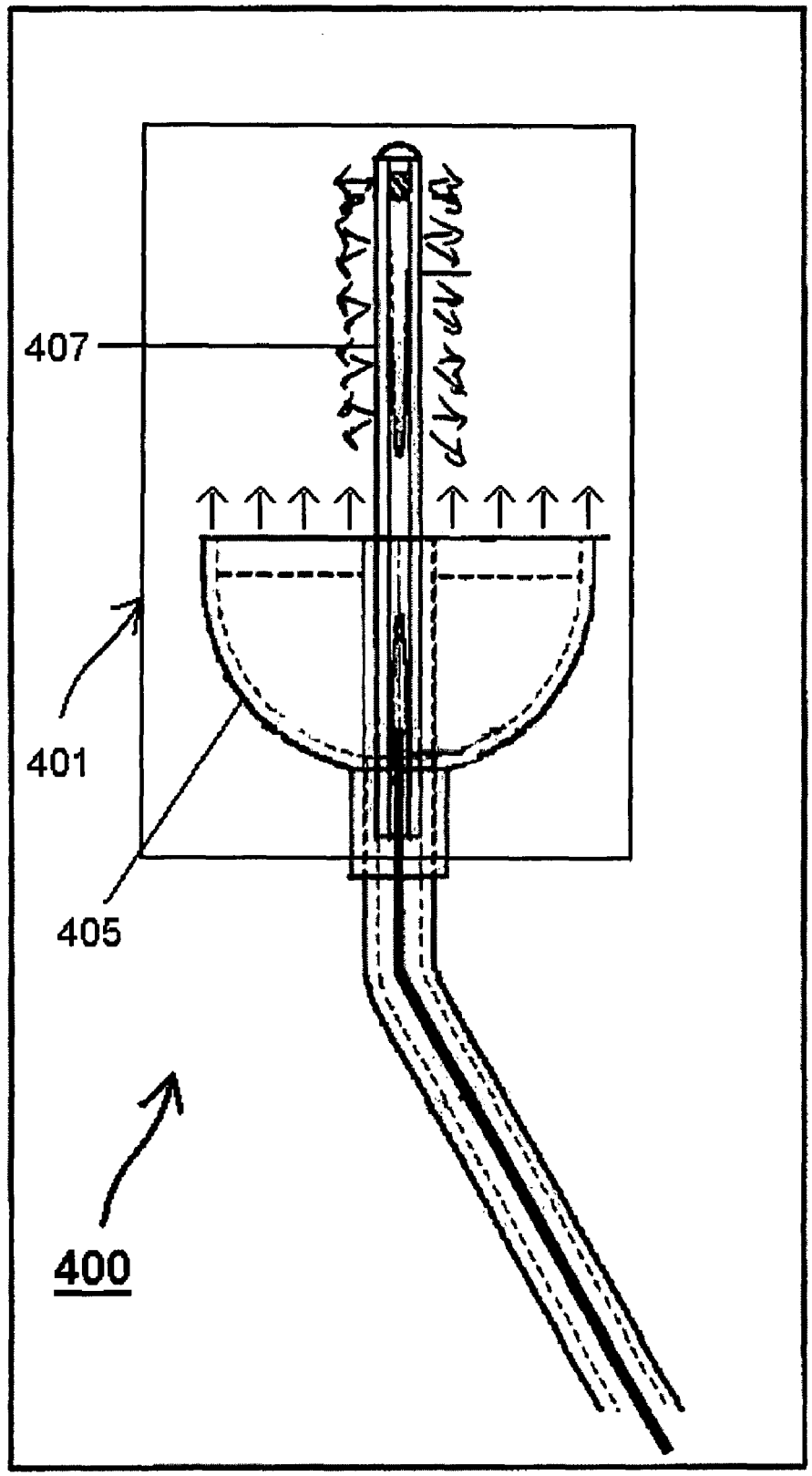
FIG. 4—illustrates the description of irradiation head.

FIG. 4 illustrates the complete description of illumination head 401 in the LED based gynecological photonic device 400. Illuminator head 401 is designed to irradiate the internal regions of the cervix, portio and the transition zone which is identified by abnormal cell growth. Illuminator head 401 is shaped in such a manner that it can easily fit into cervical region and consists of reflector 405 and cylindrical tube 407 which is inserted into the cervical opening for treating the abnormal cell presensitized with photosensitizer. Radiation from the LED source is transmitted as shown in the figure by the arrows to uniformly irradiate the transition zone, portio and cervical cells.

Figure 6:
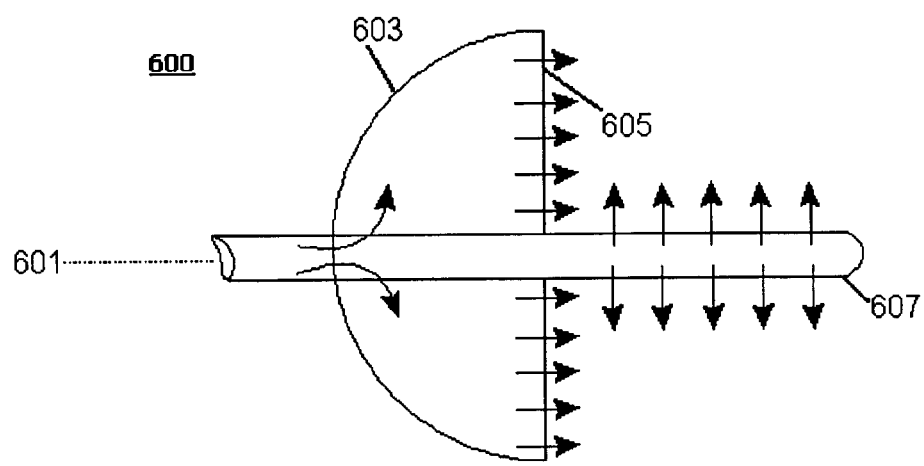
FIG. 6—depicts the drug applicator used for application of photosensitizer in the cervical and portio regions affected by abnormal cell growth.

FIG. 6 illustrates a device 600 for the application of photosensitizer as an additional preferred embodiment of the present invention. The term photosensitizer may include pro-drug, photosensitizer derivative which can be delivered using different formulation/drug delivery system like liposome, pegylation, microspheres, polymers, nano-formulation and gel formulation. The drug application device 600 can be used in combination with the illumination device. The photosensitizer can be administrated through a main channel 601 which appropriately branches off into a plurality of exit orifices, as shown by the arrows, so that the photosensitizer can be homogenously applied to abnormal cells in the portio and cervix region. Device 600 may include a hood 603 with an applicator surface 605 appropriately shaped for the portio. Tube 607 being similar in shape as to the tubes shown above would include a plurality of exit orifices also for application of the photosensitizer to the cervix channel. The photosensitizer may be included within a carrier such as a gel or liquid, for example.

In yet another embodiment instead of LED other light sources like lamps, laser or OLEDs can also be applied.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A treatment set for providing photodynamic therapy to hyperproliferative tissues in gynecological areas, comprising:
    a source of radiation;
    an applicator, said applicator having
        a shaped reflector head for applying radiation from the source to a portio area; and
        a tube comprising a tubular wall, said tube attached to said shaped reflector head and extending beyond said reflector head for a sufficient distance so as to be able to expose the cervix channel to radiation from said source;
    wherein the tube is adapted to transmit radiation from said source through the tubular wall to the cervix channel.

2. The treatment set according to claim 1, wherein said source of radiation is attached to said shaped reflector head.

3. The treatment set according to claim 1, wherein said source of radiation is located externally from said reflector head.

4. The treatment set according to claim 3, wherein said source of radiation is located in a handle which is attached to said shaped reflector head.

5. The treatment set according to claim 3, wherein said source of radiation is located externally in a unit communicating to said applicator by light guides.

6. The treatment set according to claim 1, wherein said source of radiation is selected from the group consisting of LEDs, laser diodes, and lamps.

7. The treatment set according to claim 6, wherein said LEDs are located about an inside surface of said shaped reflector head.

8. The treatment set according to claim 1, wherein said tube has a plurality of scattering centers therein for outputting said radiation.

9. The treatment set according to claim 1 wherein said applicator further is a drug applicator comprising of a semi-spherical body and cylindrical tube used for drug application into cervical and surrounding areas affected by hyperproliferative cells.

* * * * *